(12) United States Patent
Crozier et al.

(10) Patent No.: US 8,390,287 B2
(45) Date of Patent: Mar. 5, 2013

(54) COIL DECOUPLING

(75) Inventors: Stuart Crozier, Wilston (AU); Bing Keong Li, St Lucia (AU); Ewald Weber, Alexandra Hills (AU)

(73) Assignee: The University of Queensland, Brisbane (AU)

( * ) Notice: Subject to any disclaimer, the term of this patent is extended or adjusted under 35 U.S.C. 154(b) by 554 days.

(21) Appl. No.: 12/593,237

(22) PCT Filed: Mar. 26, 2008

(86) PCT No.: PCT/AU2008/000425
§ 371 (c)(1),
(2), (4) Date: Mar. 10, 2010

(87) PCT Pub. No.: WO2008/116263
PCT Pub. Date: Oct. 2, 2008

(65) Prior Publication Data
US 2010/0182009 A1    Jul. 22, 2010

(30) Foreign Application Priority Data
Mar. 26, 2007   (AU) .............................. 2007901587

(51) Int. Cl.
*G01V 3/00* (2006.01)
(52) U.S. Cl. ...................................... 324/318; 324/309
(58) Field of Classification Search .......... 324/300–322; 600/407–445
See application file for complete search history.

(56) References Cited

U.S. PATENT DOCUMENTS

| | | | |
|---|---|---|---|
| 4,825,162 A | | 4/1989 | Roemer et al. |
| 5,804,969 A | * | 9/1998 | Lian et al. ..................... 324/318 |
| 6,414,488 B1 | * | 7/2002 | Chmielewski ................ 324/311 |
| 6,492,817 B2 | * | 12/2002 | Gebhardt et al. ............. 324/318 |
| 6,657,497 B1 | * | 12/2003 | Yang et al. .................... 330/277 |
| 7,091,721 B2 | * | 8/2006 | Jevtic ............................ 324/318 |
| 7,180,291 B2 | * | 2/2007 | Chmielewski et al. ....... 324/318 |
| 7,446,528 B2 | * | 11/2008 | Doddrell et al. ............. 324/318 |
| 2005/0275403 A1 | | 12/2005 | Pinkerton et al. |
| 2012/0068709 A1 | * | 3/2012 | Crozier et al. ................ 324/318 |
| 2012/0074935 A1 | * | 3/2012 | Crozier et al. ................ 324/307 |

FOREIGN PATENT DOCUMENTS

| | | |
|---|---|---|
| JP | 08-187235 | 7/1996 |
| WO | WO 96/34397 | 10/1996 |
| WO | WO 2006/094354 | 9/2006 |

OTHER PUBLICATIONS

International Search Report, PCT/AU2008/000425 dated Jul. 17, 2008.

* cited by examiner

*Primary Examiner* — Brij Shrivastav
(74) *Attorney, Agent, or Firm* — Edwards Wildman Palmer LLP; Howard M. Gitten

(57) ABSTRACT

A Magnetic Resonance Imaging (MRI) phased array head coil (10) comprises an array of coils (1, 2, 3, 4) a decoupling circuit (7) and a decoupling base (14). Counter wound inductors from adjoining coils (1, 2, 3, 4) in the decoupling circuit (7) are interlaced to achieve mutual decoupling between adjoining coils. Each separate coil (1, 2, 3, 4) includes a pair of spaced parallel main conductors (12) located on opposite sides of a cylindrical space (5) enclosed by the coils (1, 2, 3, 4). The decoupling base (14) comprises two meandering conductor bases (8, 9) which are interlaced. Orthogonal main conductors (12) of the coil (1, 2, 3, 4) share a common conductor base (8, 9). The multiple crossings of the paths of the conductor bases (8, 9) reduces mutual coupling effects.

16 Claims, 16 Drawing Sheets

COIL DECOUPLING

FIELD OF THE INVENTION

The invention relates to an RF coil for use in a magnetic resonance imaging (MRI) system. In particular, the invention relates to a decoupling method and apparatus where coupled counter-wound inductors are used for decoupling coil elements of a MRI phased array system. The proposed decoupling method is well suited but not limited, to MRI phased array type RF coils.

BACKGROUND TO THE INVENTION

Magnetic Resonance Imaging (MRI) utilizes hydrogen nuclear spins of the water molecules in the human body, which are polarized by a strong uniform static magnetic field, the $B_0$ field. The magnetically polarized hydrogen nuclear spins generate magnetic moments and precess in the direction of the $B_0$ field and produce no useful information unless disturbed from the equilibrium state by an excitation.

The generation of a nuclear magnetic resonance (NMR) signal for MRI data acquisition is accomplished by exciting the magnetic moments with a uniform radio-frequency (RF) magnetic field, the $B_1$ field, applied transverse to the $B_0$ field. This $B_1$ field is centred at the precessional frequency of the protons (Larmor frequency) and causes some of the protons to change their spin direction by some predetermined angle. The $B_1$ field is produced by an RF transmit coil that is driven by a computer-controlled RF transmitter with a RF power amplifier. The application of the $B_1$ field has the effect of nutating the net magnetization and at the same time causes the magnetic moments to gain magnetic energy from the applied $B_1$ field. After the application of the $B_1$ field ceases, the magnetic moments revert to their ground state (through a process of free induction decay) and in doing so induce a measurable MR signal in a receiver RF coil that is tuned to the Larmor frequency. The receive RF coil can either be the transmit coil itself or an independent receive-only RF coil. The detected MR signal is processed to produce MR images by using additional pulsed magnetic gradient fields that are generated by gradient coils integrated inside the main magnet system. The gradient fields are used to spatially encode the signals and selectively excite a specific volume of the human body. There are usually three sets of gradient coils in a standard MRI system that generate magnetic fields in the same direction as the main magnetic field and vary linearly in the imaging volume.

In MRI, it is desirable for the excitation of the $B_1$ field and reception of the MR signal to be spatially uniform in the imaging volume for high quality MR images. In a standard MRI system, the transmission of the $B_1$ field is generally through the MRI system whole-body volume RF coil. This whole body RF coil, however, produces lower signal-to-noise ratio (SNR) if it is also used for the reception of the MR signal, mainly because of the large distance from the volume under imaging to the coil itself. Therefore, in order to achieve a high SNR, special-purpose RF coils are used for receiving the MR signal. In practice, a well-designed specialty RF coil has the following functional properties: high SNR, highly uniform sensitivity, high unloaded quality factor (Q) of the resonance circuit, and high ratio of the unloaded to loaded Q factors. In addition, the RF coil device must be mechanically designed to facilitate patient handling, comfort and safety. Improvement in the SNR of the detected MR signal can be achieved by using a small local coil placed close to the human body. As this local coil is placed close to the proximity of the region of interest, the small reception pattern using this local coil can focus in the region of interest thus improving the SNR. An array of these small local coils can be used to increase the coverage of the region of interest and this array system is generally referred to as phased array RF coils (see for example U.S. Pat. No. 4,825,162 assigned to General Electric Company). The outputs from the phased array system are simultaneously processed and the MR images are combined using a sum-of-square method. The phased array system obtains the high SNR and resolution of a small local coil over a large field-of-view (FOV) normally associated with body imaging but with no increase in imaging time.

In our co-pending international patent application number PCT/AU2006/000311, a focusing scheme is described for a phased array coil system that further increases the quality of image obtained. The invention is described with reference to a number of small local coils with particular application to the head and chest. The content of the co-pending application is incorporated herein by reference.

Phased array coil structures usually display strong mutual coupling between individual coil elements and some of the undesirable effects include difficulty in tuning, reduced SNR and RF field distortion causing image artefacts. Hence, minimizing the mutual coupling is known to be important to the quality of the images produced.

A number of methods have been suggested to minimize mutual coupling. Some of the known methods include the overlapping of adjacent coils (U.S. Pat. No. 4,825,162), the use of a magnetic decoupling circuit (U. S. patent application Ser. No. 2005/0275403), a degenerate birdcage coil design (U.S. Pat. No. 7,180,291), employing capacitive decoupling networks (see for example U.S. Pat. No. 7,091,721 assigned to IGC-Medical Advances Inc) and the use of low input impedance pre-amplifiers.

Another document which generally discloses the field of the invention is Japanese patent number 08-187235, assigned to GE Yokogawa Medical Syst Ltd. This patent discloses a birdcage coil for MRI having a number of diode-and-inductor in series circuits connected in parallel to capacitors in one ring of the birdcage coil so as to decouple the birdcage coil from another coil. This patent does not relate to coupled counter-wound inductors for decoupling coil elements.

There are some constraints, however, in using these decoupling methods. The overlapping of adjacent coils sacrifices the area of coverage, lumped-element decoupling networks have limitations on their decoupling power and the use of low input impedance preamplifiers can limit power transfer and limit the use of the phased array coils to receive only (i.e not suitable for transceive operation).

OBJECT OF THE INVENTION

It is an object of the present invention to provide a method of minimising coupling between coils in RF coil array systems.

Further objects will be evident from the following description.

DISCLOSURE OF THE INVENTION

In one form, although it need not be the only or indeed the broadest form, the invention resides in a decoupling circuit for an array of coil elements wherein counter wound inductors from adjoining coil elements of the array of coil elements are interlaced.

Suitably the decoupling circuit further includes current controlling capacitive circuitry.

The inductance of each inductor may suitably be adjusted to achieve mutual decoupling between adjoining coil elements.

Suitably the coil elements include main conductors which are equi-angularly spaced from the main conductors of adjoining coil elements.

The decoupling circuit may most suitably form part of one of a head coil, chest coil, extremity coil or whole body coil.

The decoupling circuit may most suitably form part of a Magnetic Resonance Imaging (MRI) phased array coil.

Suitably the decoupling circuit further includes active detuning units.

In a further form the invention resides in a coil array system comprising an array of coil elements, the decoupling circuit as defined and described hereinabove and a decoupling base comprising two or more meandering conductor bases wherein orthogonal main conductors of the coil elements share a common meandering conductor base and wherein the conductor bases are interlaced.

Suitably the conductor bases of the coil array system have inter-crossed capacitive networks at each cross-over between the conductor bases.

The conductor bases of the coil array system may most suitably follow one of a generally circular, elliptical or rectangular path.

The coil array system may most suitably form part of one of a head coil, chest coil, extremity coil or whole body coil.

The coil array system may most suitably form part of a Magnetic Resonance Imaging (MRI) phased array coil.

In yet a further form the invention resides in a decoupling base for an array of coil elements, comprising two or more meandering conductor bases wherein orthogonal main conductors of the coil elements share a common meandering conductor base and wherein the conductor bases are interlaced.

Suitably the conductor bases have inter-crossed capacitive networks at each cross-over between the conductor bases.

Suitably the conductor bases follow one of a generally circular, elliptical or rectangular path.

The conductor base may most suitably form part of one of a head coil, chest coil, extremity coil or whole body coil.

The conductor base may most suitably form part of a Magnetic Resonance Imaging (MRI) phased array coil.

In still a further form the invention resides in a method of minimizing coupling between coil elements in a coil array system by incorporating counter wound inductors in a circuit of each coil element of the coil array system and adjusting the inductance of each inductor until coupling between coil elements is minimised.

Preferably the method further includes the step of connecting coil elements of the coil array system with a decoupling base of two or more meandering conductor bases wherein orthogonal main conductors of the coil elements share a common conductor base.

BRIEF DETAILS OF THE DRAWINGS

To assist in understanding the invention preferred embodiments will now be described with reference to the following figures in which.

Figure 15:
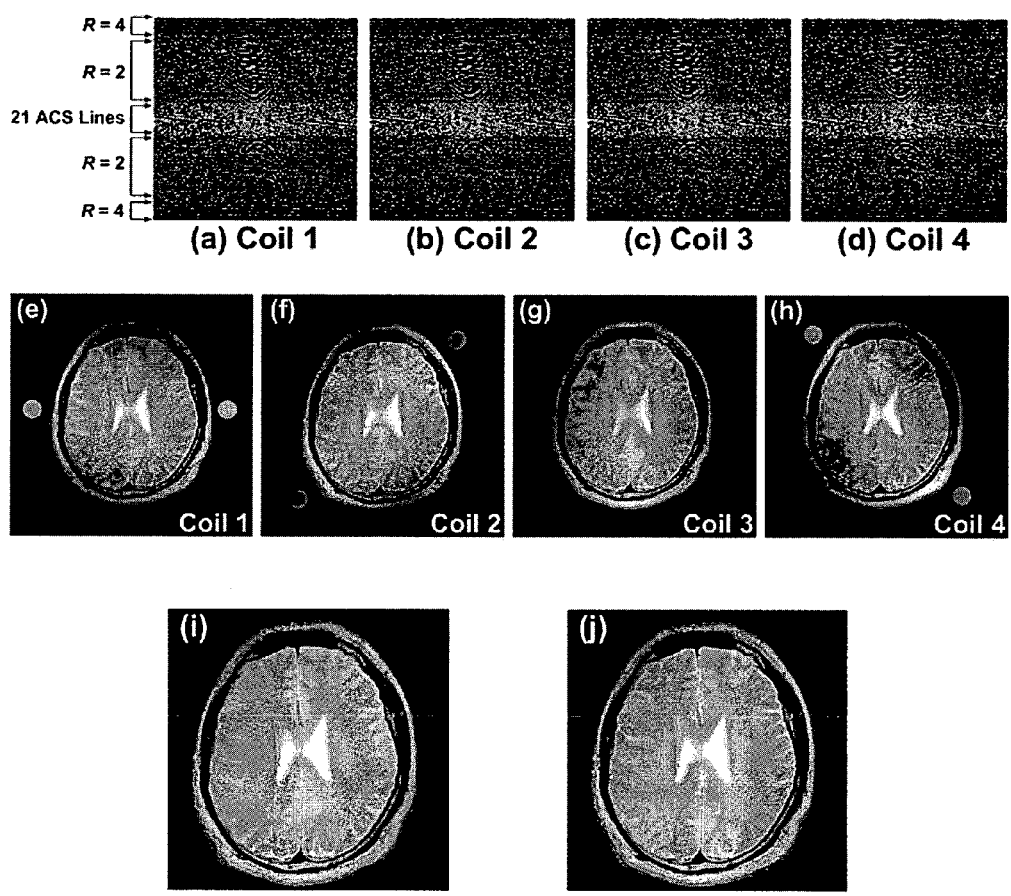

FIG. 15 (a-d) is the four set of reduced k-space data using variable reduction factors (R) of 4 and 2 with 21 ACS lines at the centre of the k-space data, (e-h) are the four set of VD-GRAPPA reconstructed brain images corresponding to each coil element, (i) is the composite brain image after applying a sum-of-square on the four VD-GRAPPA reconstructed brain images as shown in (e-h), and (j) is the same composite brain image obtained from applying a sum-of-square on four fully acquired k-space data.

DETAILED DESCRIPTION OF THE DRAWINGS

In describing different embodiments of the present invention common reference numerals are used to describe like features. For ease of understanding the following description is in relation to the application of the invention to a Rotary Phased Array (RPA) Head Coil. However, the invention is not limited to this specific application. As explained in our co-pending application (PCT/AU2006/000311), the invention can be applied to other coil arrangements. The RPA head coil has been numerically modelled and a prototype constructed as described below.

Figure 1:
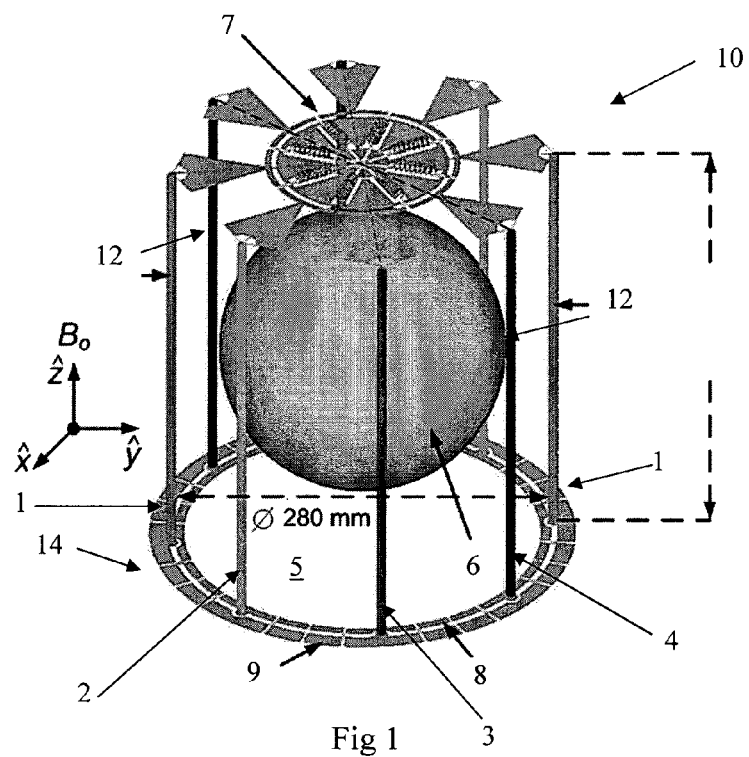
FIG. 1 depicts a 4-element rotary phased array head coil with a counter wound inductor decoupling circuit and a decoupling circular conductor base.

A coil array system in the form of the RPA head coil 10 consists of an array of coil elements in the form of four separate coils 1, 2, 3, 4 arranged in a rotary structure as shown in FIG. 1. (Persons skilled in the art will understand that FIG. 1 is an illustrative representation of the concept only, not the actual design of the prototype RPA-head coil). The concept of the RPA head coil 10 is that each separate coil 1,2,3,4 of the rotary head coil 10 has a pair of main conductors 12 extending parallel to the direction of the main magnetic field ($B_0$ field) and located on opposite sides of a cylindrical space 5 enclosed by the coils 1,2,3,4. The coils 1,2,3,4 are mutually decoupled, spaced equi-angularly around the cylindrical space 5 with the angle between the nearest neighbouring coil being 180°/N, where N is the number of coils, and are each located in a respective diametric plane of the cylindrical space. The main conductors 12 of each coil 1,2,3,4 will carry equal currents but in opposite directions and with such a distribution of currents on the main conductors 12, each coil 1,2,3,4 will produce a plane of maximum sensitivity along the axis of the cylindrical space 5. That is, the plane of sensitivity of each coil 1,2,3,4 will cut radially or diametrically through the cylindrical space 5 rather than wrap circumferentially around the cylindrical space. Therefore, the sensitivity deep at the centre of the RPA head coil 10 will be improved.

Numerical Modelling

Based on a conceptual consideration of the operation of the rotary phased array head coil 10, a combined hybrid method of moments (MoM)/finite element method (FEM) method is employed for modeling and analysis. The MoM/FEM software is commercially available from FEKO (available from EM Software & Systems-SA (Pty) Ltd of Technopark, Stellenbosch, South Africa; www.feko.info).

A full-wave MoM-based RF simulation program, is employed for the design and modelling of the receive-only 2 T 4-element RPA head coil 10. Hybrid MoM/FEM is also used to investigate the feasibility in using such a coil structure to improve the sensitivity deep in the centre of the rotary head coil 10. The rationale in using hybrid MoM/FEM method is that this method exploits the benefits from both techniques, whereby FEM can efficiently be used for the treatment of dielectric samples while MoM can be efficiently used for the modelling of RF coils and the treatment of the open boundary radiating coil structures. In addition, the hybrid MoM/FEM method fully accounts for both the coupling between coils 1,2,3,4 and dielectric sample-coil coupling by applying MoM as the radiation boundary for the FEM. Therefore, the hybrid MoM/FEM method forms an exceptionally capable full-wave numerical technique, which is particularly suited for the design of MRI RF-coils and RF field behaviour analysis.

Depicted in FIG. 1 is the designed and modelled 4-element rotary phased array head coil 10. A homogenous spherical phantom 6, 210 mm in diameter, with dielectric properties of $\sigma=0.6$ S/m and $\in_r=48.6$, which approximately resemble a human head, is also modelled for loading purposes. (This spherical phantom is modelled accordingly to the real phantom that is later used in the MRI experiment for imaging purposes).

Counter Wound Inductor Decoupling Circuit

In designing the RPA head coil 10, it is clear that all coils 1,2,3,4 of the array of coils have to be mutually decoupled. As mentioned, coil elements positioned orthogonal to each other are naturally decoupled. However, for coil elements that are located off orthogonal to each other, some decoupling methods have to be advocated to minimize the mutual coupling. Due to the geometric arrangements of the coils 1,2,3,4 of the rotary head coil 10, the use of an overlapping method is not possible. Capacitive decoupling networks do not have sufficient decoupling power to decouple the strong mutual coupling between off-orthogonal coil elements and the use of low input impedance preamplifiers will limit power transfer and restrict the adaptation of the RPA head coil 10 to be used as a transceiver coil. In view of this, a counter wound inductor decoupling circuit is proposed. The decoupling circuit 7 has been integrated onto the top portion of the RPA-head coil 10 as show in FIG. 1. The decoupling circuit uses coupled counter wound inductors to achieve mutual decoupling.

The RPA head coil 10 is designed to have an effective cylindrical space of 280 mm in diameter and a height of 320 mm. To preserve the symmetry and maintain an equal distance of 280 mm between two main conductors 12 of each coil 1,2,3,4, two independent conductor bases 8,9 have been designed and modelled, as shown in FIG. 1 and described in more detail by reference to FIG. 4. Since Coil 1 and Coil 3 are geometrically positioned orthogonally to each other, they are naturally decoupled and therefore share the same circular conductor base 8. Similarly, Coil 2 and Coil 4, which are geometrically positioned orthogonally to each other as well, share the other circular conductor base 9.

Shown in FIG. 2 is a counter wound inductor decoupling circuit according to one embodiment of the invention. The circuit is shown conceptually in FIG. 2(*a*).

Referring to FIG. 2(*b*), the currents of the two main conductors 12 of each coil 1,2,3,4 are divided and directed into four decoupling inductors, denoted as L in FIG. 2(*b*). The capacitors, denoted as C in FIG. 2(*b*), allow tuning of the coil element to the resonance frequency and concurrently control the current distributions to the four decoupling inductors L, which further aid in minimizing the mutual coupling. For the counter wound inductor decoupling circuit to achieve mutual decoupling between coils, the four decoupling inductors on each coil 1,2,3,4 are coupled with the counter-wound inductors of the next-neighbouring coil 1,2,3,4 by interlacing the inductors L together as shown in FIG. 2(*c*) and photograph FIG. 2(*d*) to form counter-wound decoupling inductor pairs 20.

This interlacing of the counter-wound inductors L of each coil 1,2,3,4 with the inductors L of its adjacent coil 1,2,3,4 is repeated for all the coils 1,2,3,4 until all the counter-wound inductors L of each coil are interlaced with an adjoining inductor L of an adjacent coil 1,2,3,4. Adjusting the interlacing distance alters the coupling between the inductors and in this way, mutual coupling that existed between coils 1,2,3,4 of the RPA head coil 10 is minimized.

Reference is made to FIG. 2(*e*) to further clarify the operation of the proposed coupled counter wound inductors decoupling circuit. Depicted in FIG. 2(*e*) is the equivalent schematic diagram of FIG. 2(*b*) of a single coil element, in this case in the form of coil 1 of the RPA head coil 10. In the schematic diagram of FIG. 2(*e*), the coil 1 consists of two main conductors denoted as LR1A and LR1B. The capacitors that are used for controlling the current distribution to the decoupling inductors are denoted as Cdec1_4 and Cdec1_2. All other capacitors denoted as C are used for tuning. Ldec1_2 and Ldec1_4 are the decoupling inductors. As can be seen from this schematic diagram, the currents from the two main conductors, LR1A and LR1B, are divided and directed into four decoupling inductors Ldec1_2 and Ldec1_4. In addition, the decoupling inductors, Ldec1_2 and Ldec1_4 are wound in the opposite direction, that is if Ldec1_2 is wound in the clockwise direction, then Ldec1_4 must be wound in a counterclockwise direction, and vice versa. Once the direction of the winding for Ldec1_2 and Ldec1_4 has been determined, the decoupling inductors on other coils 2,3,4 will follow the same direction of wounding as shown in FIG. 2(*f*). In this way, the decoupling inductors of each coil 1,2,3,4 are counter wound from each other and can then be interlaced or coupled together.

For example, from FIG. 2(*f*), for coil 1 to be decoupled from coil 2 and coil 4, which are the next neighbouring coils with respect to coil 1, the decoupling inductors Ldec1_2 and Ldec1_4 of coil 1 are coupled to the counter wound inductors of coil 2 and coil 4, which are denoted as Ldec2_1 and Ldec4_1 respectively. Hence, Ldec1_2 and Ldec2_1 will form a pair of coupled counter wound inductors and Ldec1_4 and Ldec4_1 will form another pair of coupled counter wound inductors, which can then mutually decouple coil 1 from coil 2 and coil 4. A similar organisation of pairing counter wound inductors follows for decoupling the rest of the coil, that is, LdecX_Y is paired with LdecY_X, LdecX_Z is paired with LdecZ_X, where X is the index number of one coil, Y and Z are the index number of the next neighbouring coils that X is to be decoupled from. For the example, if coil 3 is to be mutually decoupled, the next neighbouring coil with respect to coil 3 is coil 2 and coil 4. Hence, X=3, Y=2, Z=4 and in this case, the counter wound inductors of Ldec3_2 is paired with Ldec2_3, Ldec3_4 is paired with Ldec4_3 as indicated by the bi-direction arrows in FIG. 2(f). FIG. 2(g) shows the complete schematic diagram of RPA head coil 10.

Active Detuning

Figure 3:
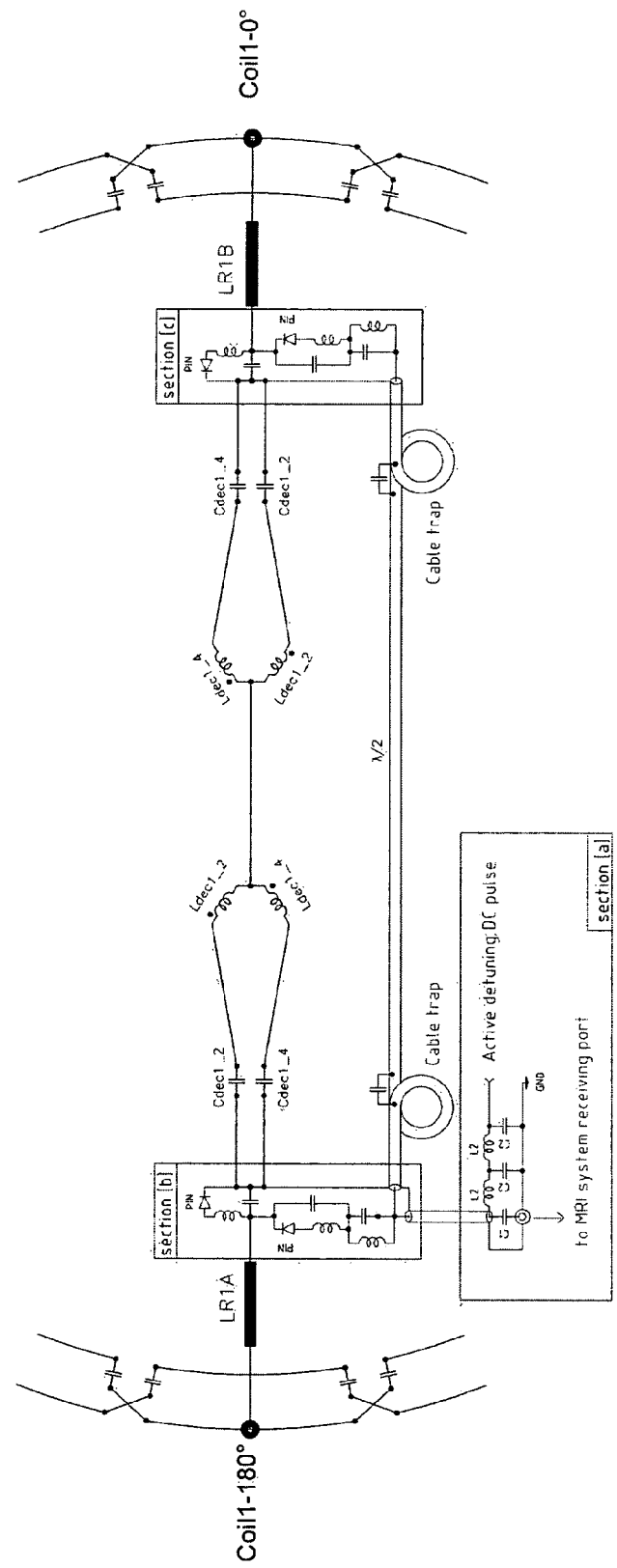
FIG. 3 depicts an active detuning circuit.

Referring to FIG. 3, two active detuning units are incorporated in every coil 1,2,3,4 of the rotary phased array head coil 10. (Coil 1 is shown in FIG. 3). The active detuning units are used to properly detune (practically make the rotary phased array coil invisible to the MRI system) during the transmission of the RF excitation pulse. Like all receive-only MRI coils, the rotary phased array head coil 10 must be properly detuned, otherwise it will adversely affect the homogeneity of the transmit RF excitation pulse. In addition, during the transmission of the RF excitation pulse, the active detuning units will further prevent any induced current from flowing into the receiving ports of the MRI system, protecting the sensitive preamplifiers of the MRI system. Hence, proper designing of the active detuning circuitry is important. An active detuning DC pulse (generally +5V to −30V) is used to activate the detuning circuit and switching of this DC pulse is synchronised with the transmission timing of the RF excitation pulse.

In the active detuning circuit used shown in FIG. 3, the common or traditional use of an additional DC line, with wires normally connected directly to an active detuning circuit attached to a RF coil, is not necessary. This has the advantage of increasing the safety aspects in favour to patients undergoing a MR imaging process.

To understand how the active detuning circuit works, reference is made to FIG. 3, starting with section [a], when the active detuning DC pulse is switched on (+5V), the capacitor (C1) will block any DC current from flowing into the RF receiving port of the MRI system. Following the path of the DC current into the active detuning circuits, sections [b] and [c] (note that section [c] is an exact replica of [b]), the DC current will split equally via the half wavelength cable trap co-axial cable and into the two active detuning circuits and cause the PIN diodes to turn on, forming a short circuit. By forming a shorted path, the inductor and capacitor that are connected with a particular diode form a parallel LC unit, which is equivalent to an open circuit at the resonance frequency (note that the values of the inductor and capacitor are calculated such that they will form an open circuit at a particular operating frequency, in this case 85 MHz). This will cause each coil 1,2,3,4 of the rotary phased array head coil 10 to virtually become an open circuit, thus during the transmission of the RF excitation pulse, the switched off rotary phased array head coil 10 will prevent the homogeneity of the transmitted RF field being distorted. Also, any current on the coil element induced by the transmitted RF excitation pulse will be prevented from flowing into the receiving port of the MRI system, protecting the preamplifiers of the MRI system. In addition, the half a wavelength cable trap co-axial cable, further minimises any standing wave induced on the co-axial cable, which prevents distortion to the transmit RF field and also makes the head coil 10 safer for the patient.

During receiving or detecting of the MR signal, the polarity of the DC pulse is reversed (to −30V). The received MR signal on both sections [b] and [c] is too weak to turn the blocked PIN diodes on; hence the received MR signal will flow directly into the receiving port of the MRI system. The MR signal received at section [c] is 180° phase shifted via the half wavelength cable trap co-axial cable, then combined together with the MR signal received at section [b]. The combined MR signal will then go into the receiver port of the MR system. At section [a], the two inductors and two capacitors (denoted as L1 and C2) act as a RF choke blocking the detected MR signals from flowing into the active detuning DC pulse source.

Circular Decoupling Base

Figure 4:
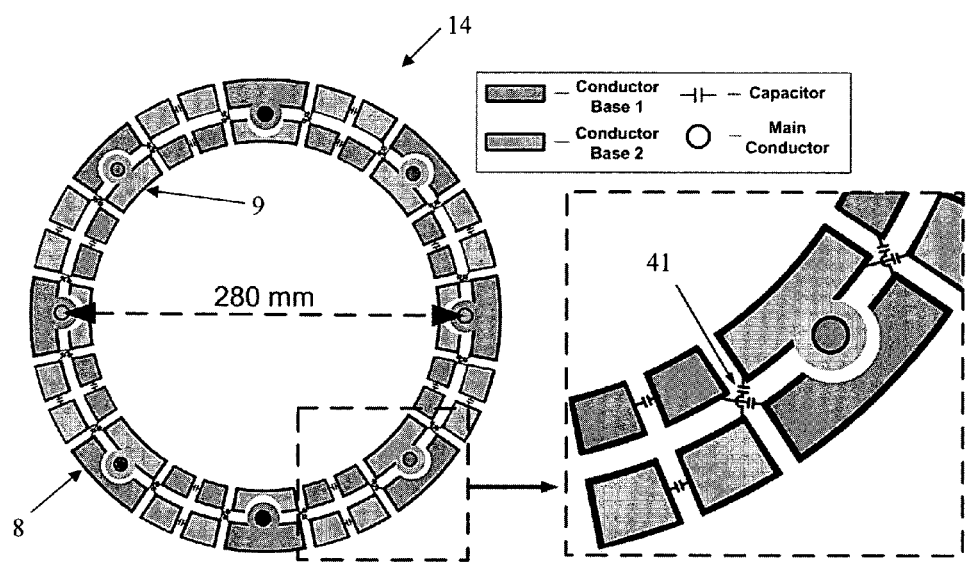
FIG. 4 depicts details of the decoupling circular conductor base.

The decoupling base 14 shown in FIG. 1 is shown in greater detail in FIG. 4. The decoupling base 14 comprises two generally circular conductor bases 8 and 9. It can be observed that using the two specially designed circular conductor bases 8,9, all the main conductors 12 of each coil 1,2,3,4 are ensured to be 280 mm apart and coils that are positioned orthogonal to one another share the same conductor base. In addition, the two conductor bases 8,9 are interlaced with one another, to form a meandering conduction path similar to a pair of twisted wires. The interlacing of the conduction path cancels coupling between the two conductor bases 8,9. The interlacing of the two conductor bases 8,9 is achieved by using inter-crossed capacitors 41 at each cross-over, as shown in the enlarged portion of FIG. 4.

Figures 2A, 2B:
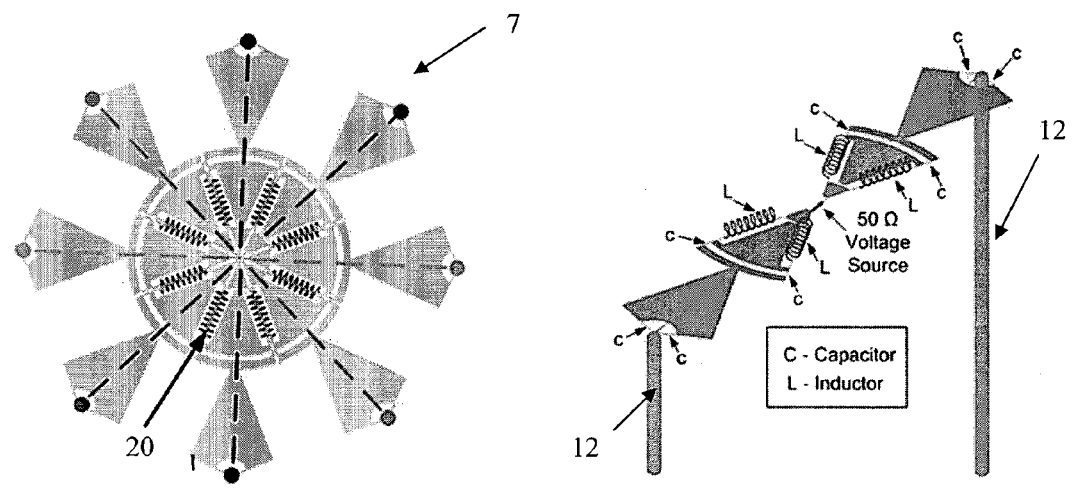
FIG. 2 depicts details of the counter wound inductor decoupling circuit.
Figure 2C:
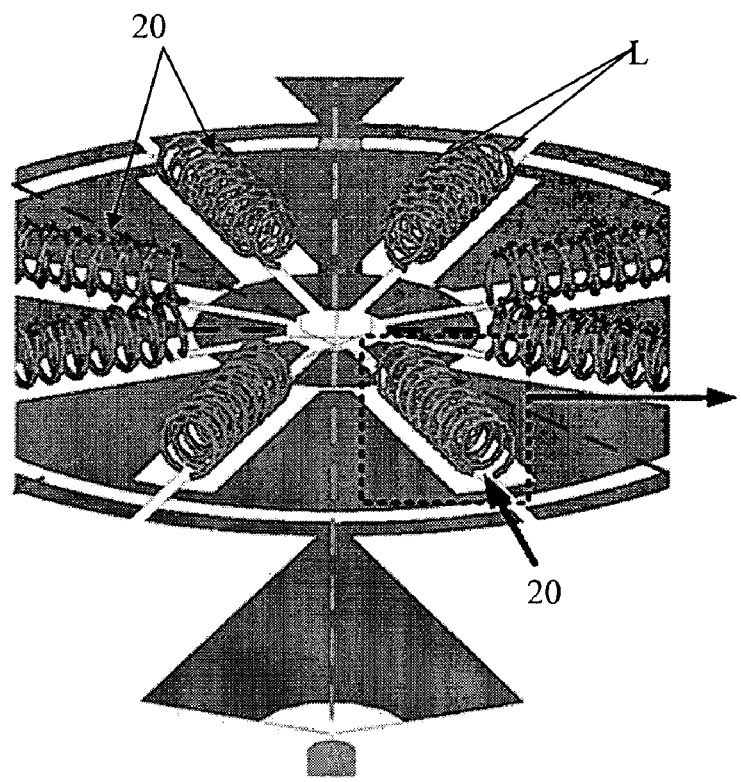
Figure 2D:
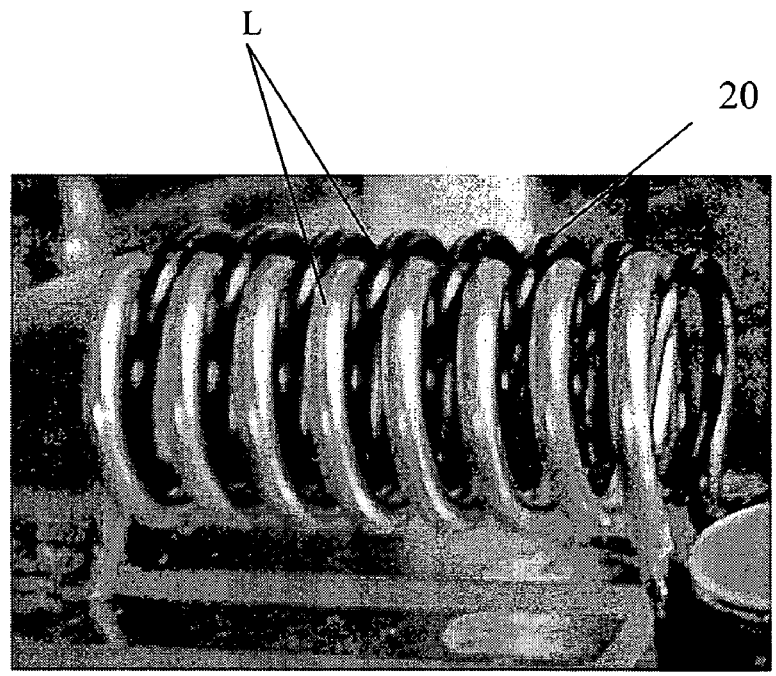
Figure 2E:
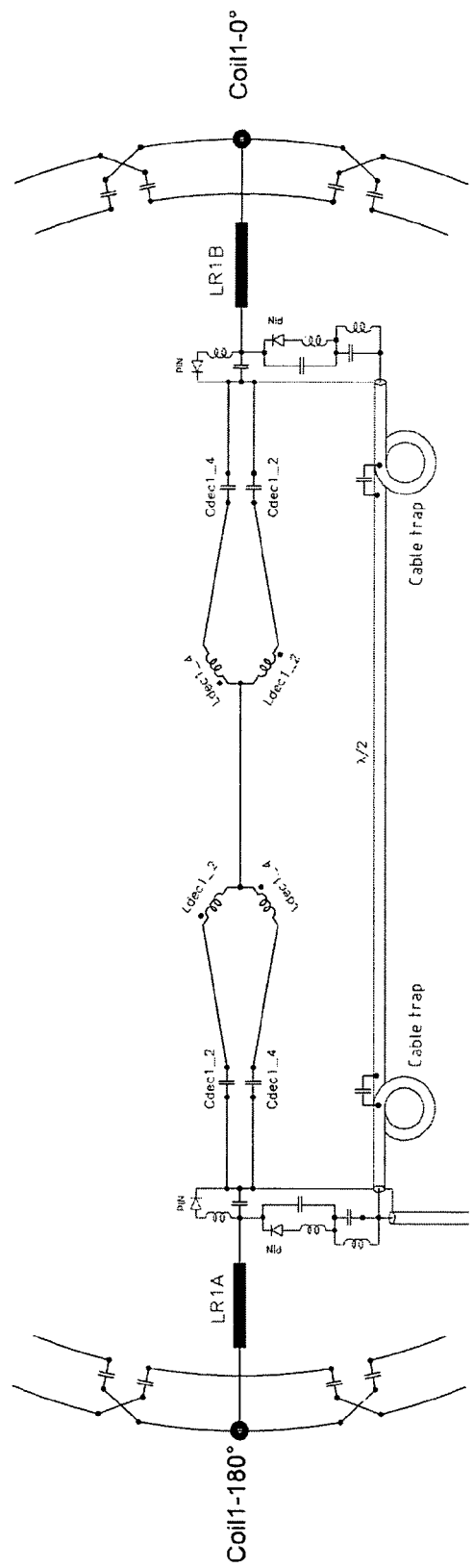
Figure 2F:
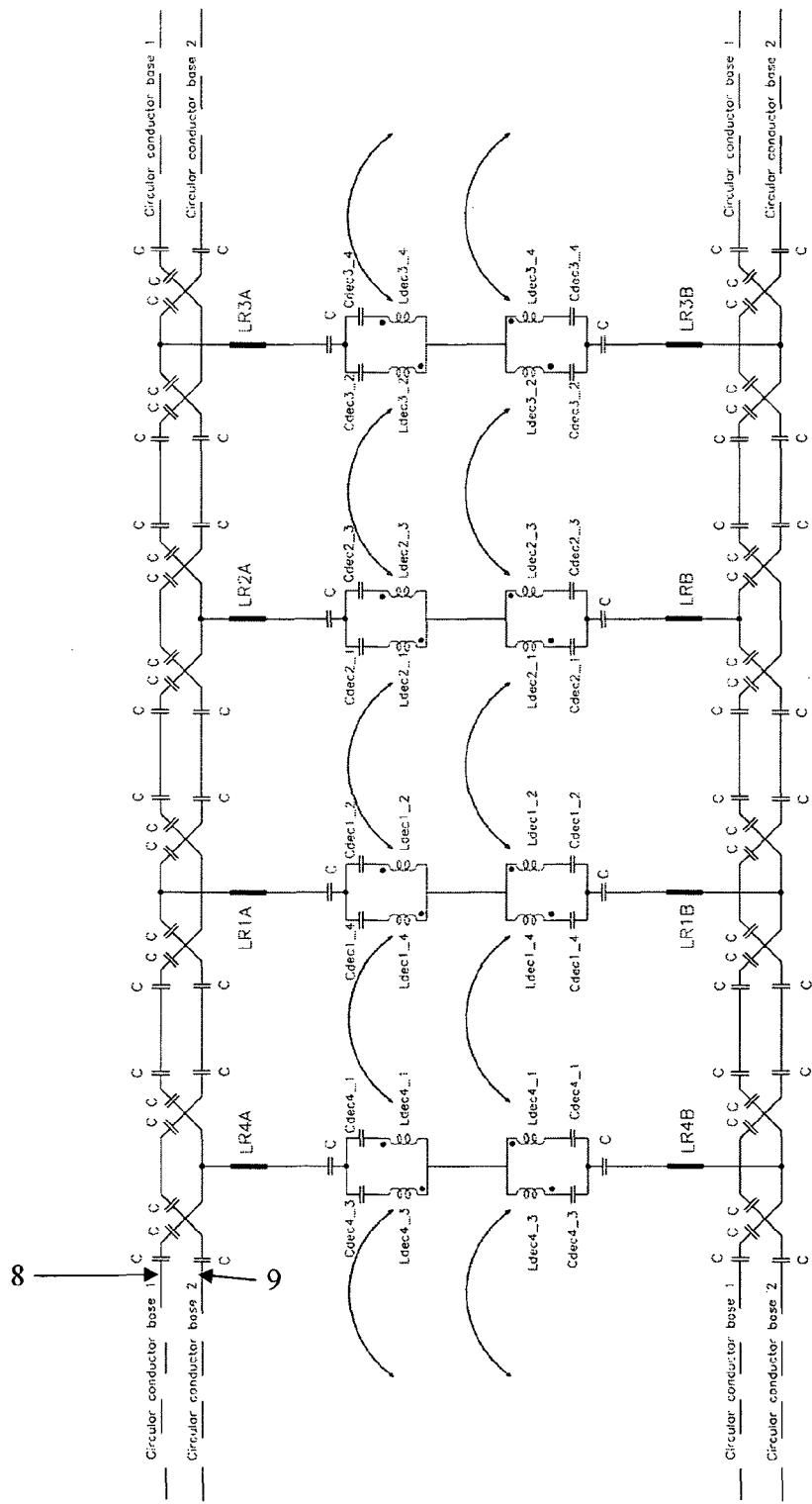
Figure 2G:
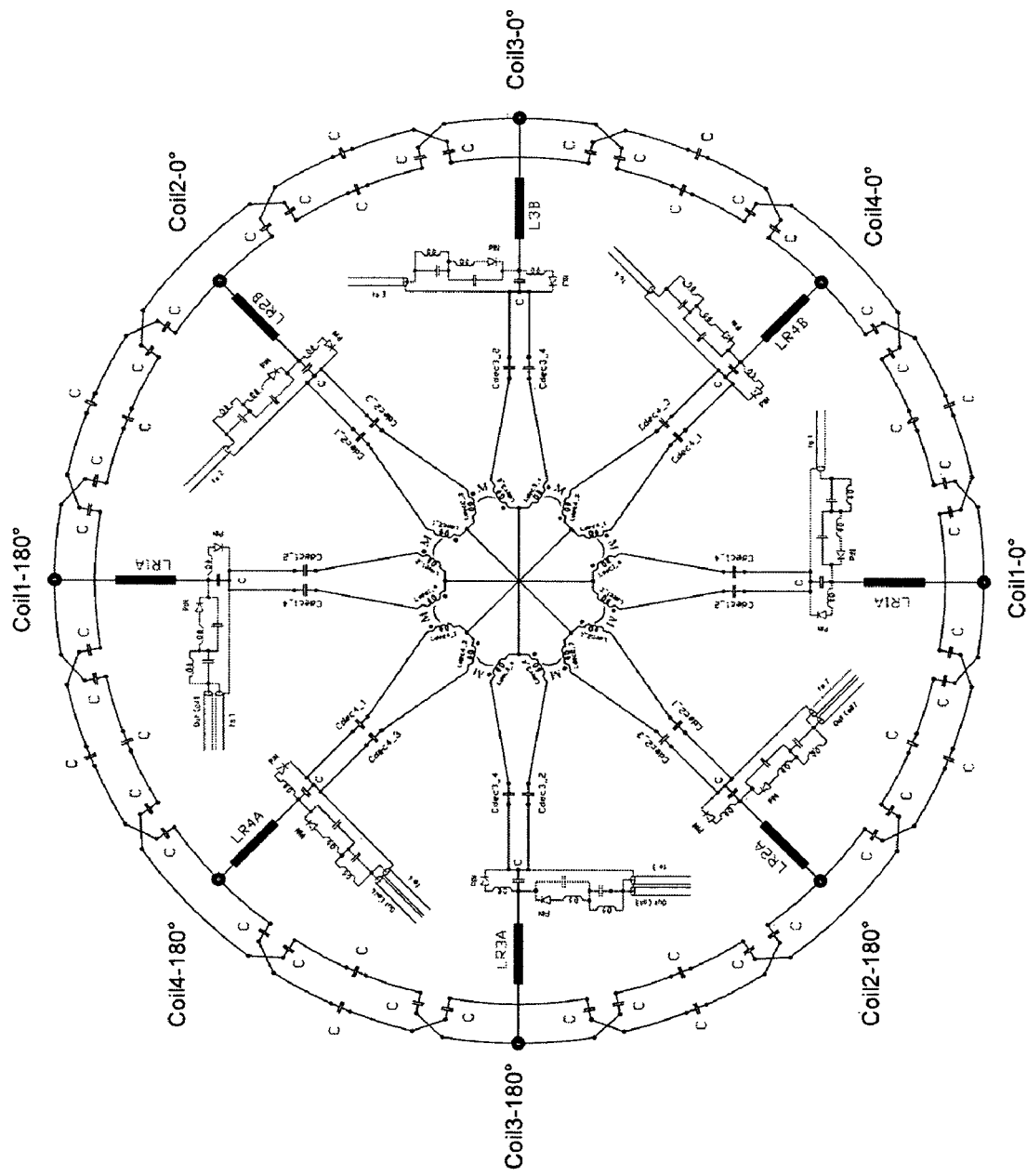

The arrangement is also depicted in FIG. 2(f). From FIG. 4 and FIG. 2(f) it can be seen that one conductor base 8 connects coil 4 and coil 2 and another conductor base 9 connects coil 1 and coil 3. The multiple crossings of the conductor base path reduces mutual coupling effects.

Persons skilled in the field will appreciate that the number of conductor bases will increase with the number of coils. So, clearly, six coils will require 3 conductor bases, eight coils will require 4 conductor bases, etc. It will also be evident that the circular path is merely for convenience. Other paths, such as elliptical or rectangular, will be suitable for other coil array systems. For instance, an elliptical path will be suitable for a chest coil array.

Demonstration

To demonstrate that the counter wound inductor decoupling circuit can achieve mutual decoupling, the RPA head is firstly numerically modelled using a hybrid MoM/FEM method. Each coil 1,2,3,4, with the proposed decoupling system as shown in FIG. 1 and loaded with the spherical phantom, is independently tuned to the resonance frequency of 85 MHz at 2 T and matched to the system impedance of 50Ω. In the hybrid MoM/FEM method, this is done by exciting the coil 1,2,3,4 with a 50Ω voltage source and calculating the $S_{11}$ response (note that the hybrid MoM/FEM package used in the demonstration allows the calculation of $S_{11}$ response). Once tuning and matching has been achieved, the counter wound inductor decoupling circuit on each of the coils 1,2,3,4 are thereafter coupled together with the next neighbouring coils' inductors. $S_{11}$ response for each individual coil 1,2,3,4 (this time with one coil excited with a 50Ω voltage source while the other three coils are individually connected to a 50Ω load) is again calculated to check for successful mutual decoupling between coils 1,2,3,4. Evidence of mutual coupling between coils 1,2,3,4 is, however, visible if a dual minimum or a 'splitting' of the calculated $S_{11}$ response is observed. In this case, the interlacing distance between inductors is adjusted, $S_{11}$ response recalculated, until no splitting of the $S_{11}$ response is observed and the coils 1,2,3,4 are mutually decoupled. This decoupling procedure is repeated for each coil 1,2,3,4.

Once the mutual decoupling of each coil 1,2,3,4 has been achieved, the magnetic fields inside the spherical phantom with an axial plane (xy plane) profile, located at the mid section are calculated. The four magnetic field profiles that correspond to each individual coil 1,2,3,4 of the modelled RPA-head coil 10 are calculated by exciting one coil with a 1V, 0° voltage source while terminating the other three coils with a 50Ω and vice versa. Following the principle of reciprocity [Hoult, Concepts Magn Reson 12(4) pg 173-187, 2000], the transmission fields $\hat{B}_{1t}^{+}$ and reception fields $\hat{B}_{1r}^{-}$ can then be calculated by [Collins & Smith Magn Reson Med 45(5) pg 684-691, 2001]

$$\hat{B}_{1t}^{+} = \frac{(\hat{B}_x + i\hat{B}_y)}{2} \quad [1]$$

$$\hat{B}_{1r}^{-} = \frac{(\hat{B}_x - i\hat{B}_y)^{*}}{2} \quad [2]$$

where $\hat{B}_x$, $\hat{B}_y$ are the two orthogonal components of the complex magnetic fields calculated by the hybrid MoM/FEM method; an asterisk denotes a complex conjugate. Solving Eqs [1] and [2], we obtain the transmission and reception $B_1$ fields, from which signal intensity (SI) profiles corresponding to each coil 1,2,3,4, can be calculated by [Collins & Smith Magn Reson Med 45(5) pg 684-691, 2001]

$$SI = i\omega M_O \sin^n(\kappa \gamma \tau |\hat{B}_{1t}^{+}|)|\hat{B}_{1r}^{-*}| \quad [3]$$

where ω is the operating frequency, $M_0$ is the initial magnetization, γ is the gyromagnetic ratio, τ is the RF pulse duration of the transmission field, κ is a dimensionless constant to adjust the flip angle and the integer n is sequence-dependent and is set to 3 for spin echo sequences. The hybrid MoM/FEM calculated SI profiles and the MR images of the spherical phantom (shown later in the result section) acquired in parallel using the prototype RPA-head coil 10, constructed accordingly to the hybrid MoM/FEM modelled rotary head coil, are used to show that the counter wound inductor decoupling circuit 7 is capable of effectively minimising mutual coupling between coils 1,2,3,4 and that the RPA-head coil 10 provides improved sensitivity deep at the centre of the effective coil volume.

Prototype

Figures 5, 6:
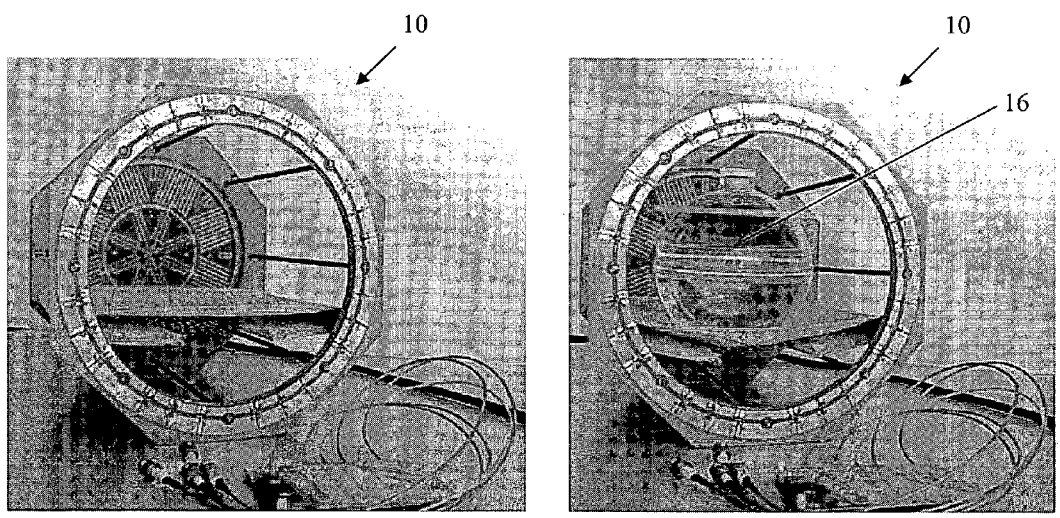
FIG. 5 depicts a prototype RPA head coil incorporating an embodiment of the invention.
FIG. 6 depicts the prototype RPA head coil of FIG. 5 loaded with a spherical phantom.
Figure 7A:
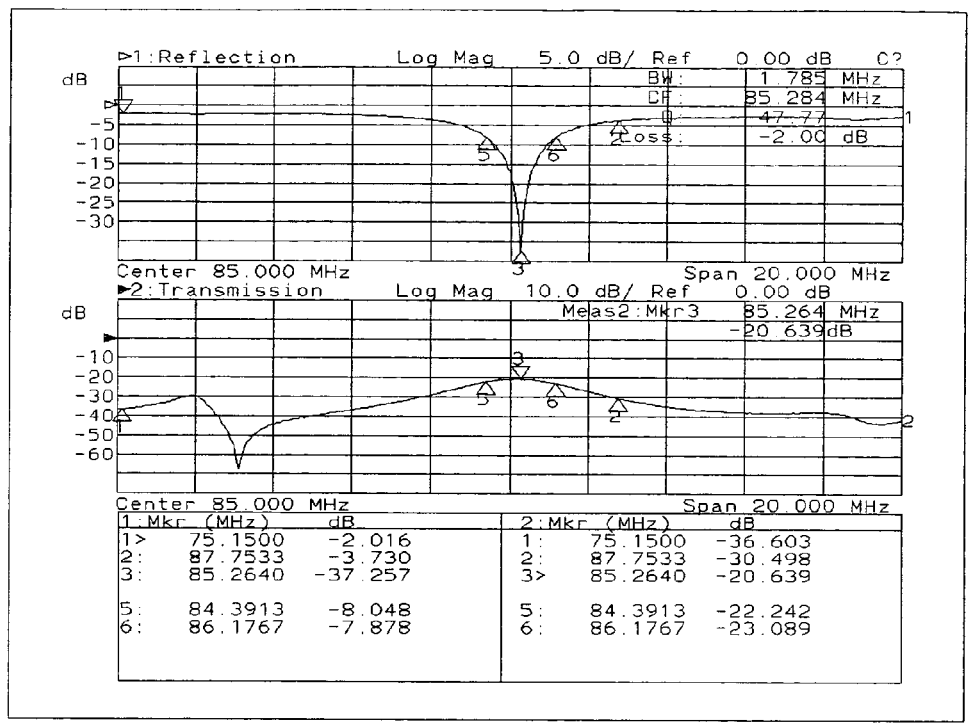
FIG. 7 (a-c) show screenshots of the measured S-parameters for Coil 1 connected to the reflection port, while Coil 2, Coil 3 and Coil 4 are (one after the other) being connected to the transmission port of an analyzer.
Figure 7B:
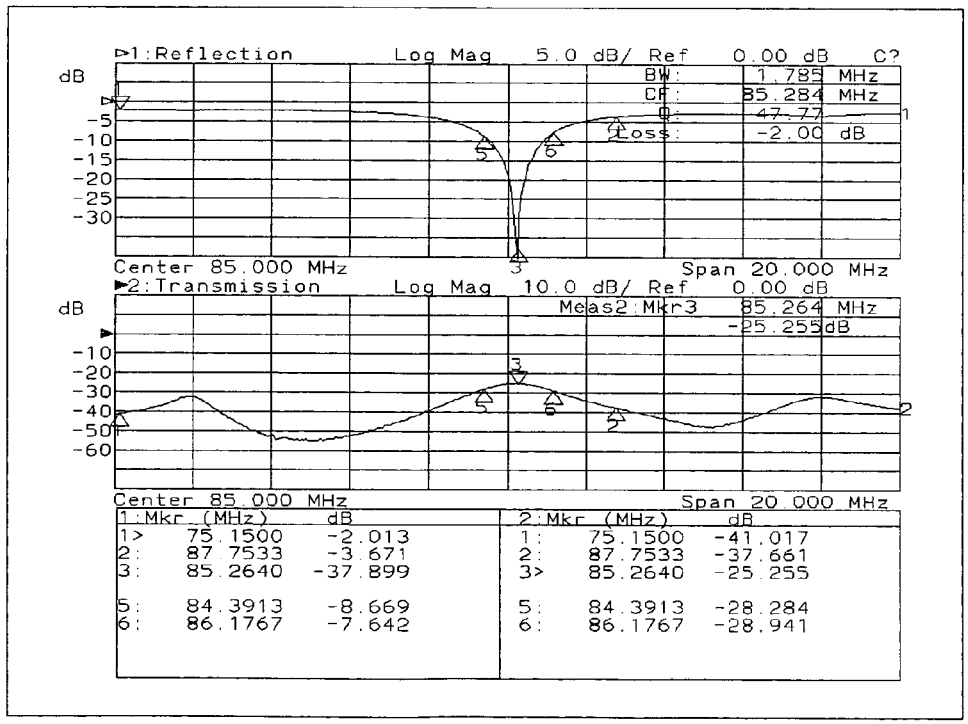
Figure 7C:
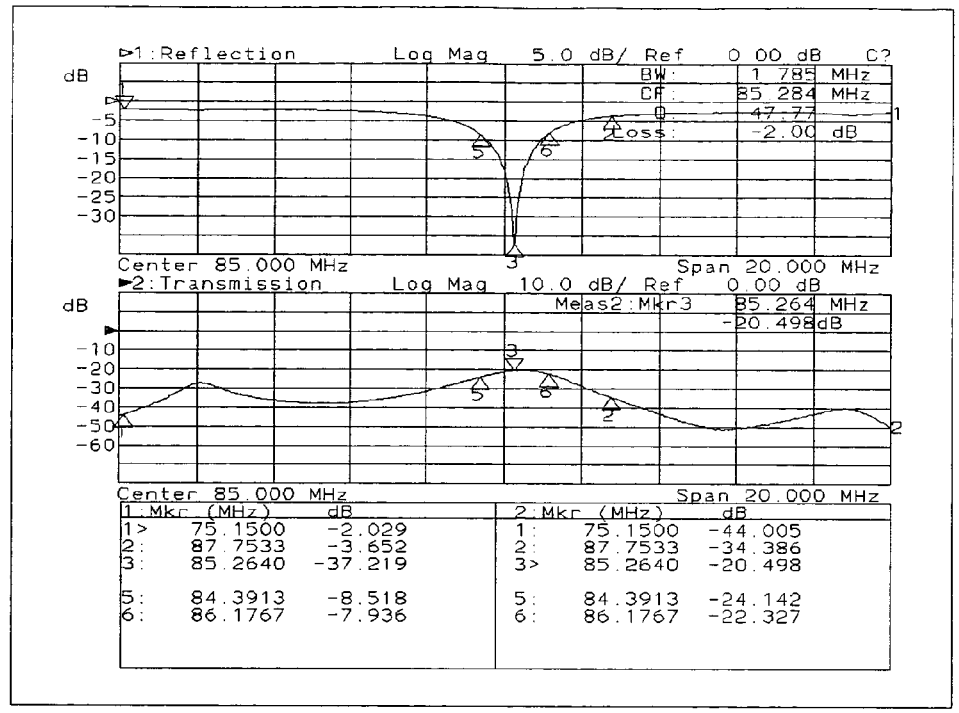
Figure 8A:
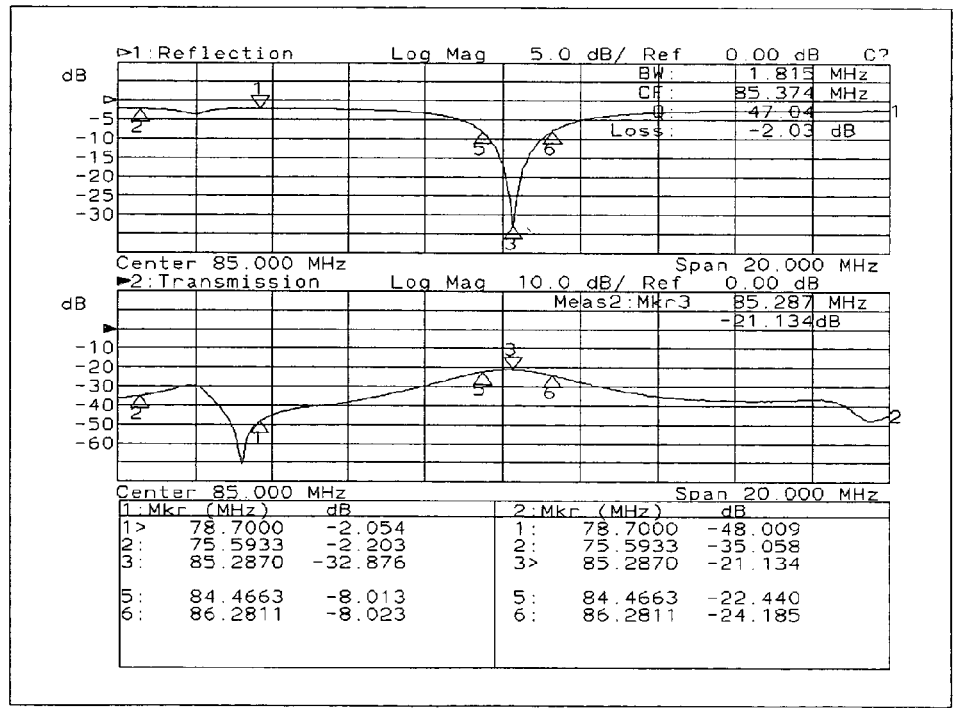
FIG. 8 (a-c) show screenshots of the measured S-parameters for Coil 2 connected to the reflection port, while Coil 1, Coil 3 and Coil 4 are (one after the other) being connected to the transmission port of an analyzer.
Figure 8B:
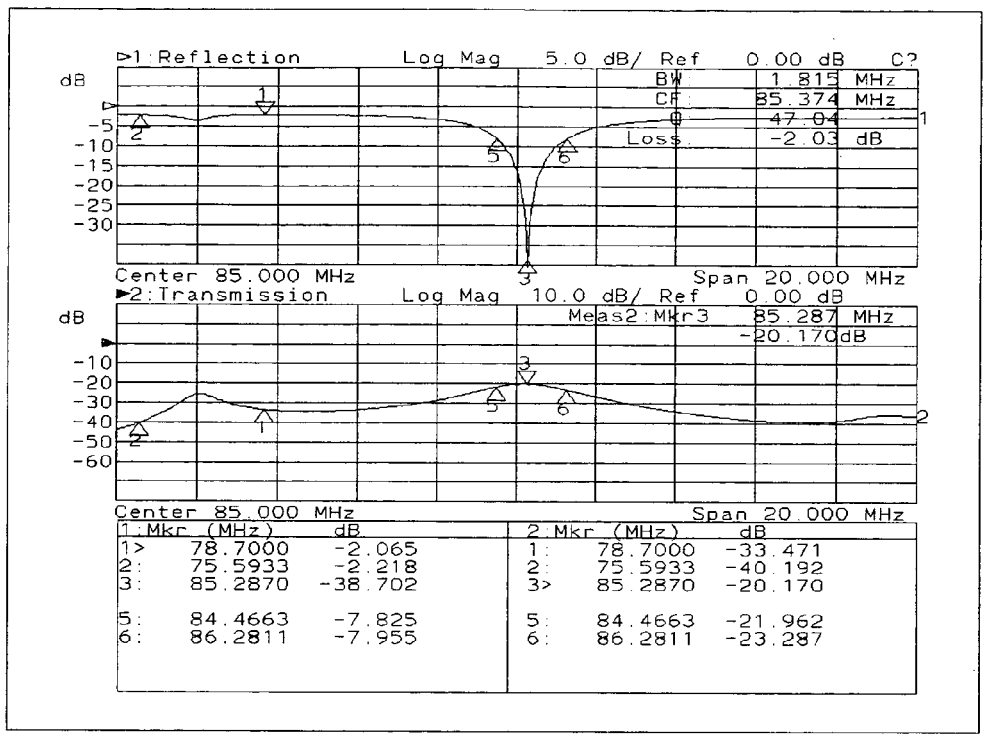
Figure 8C:
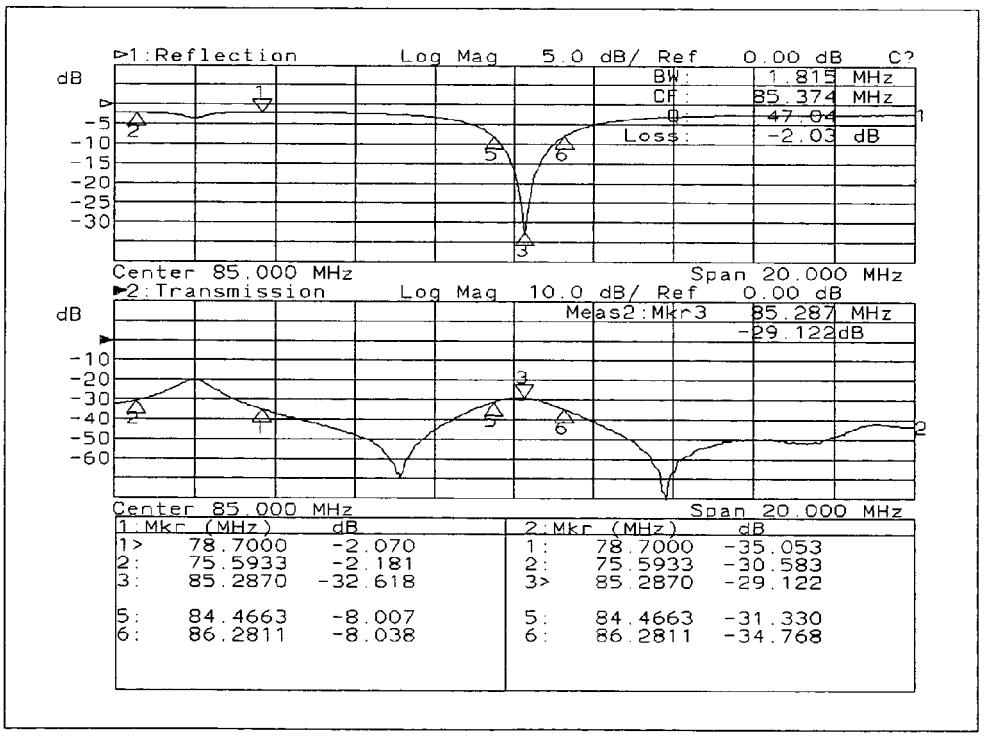
Figure 9A:
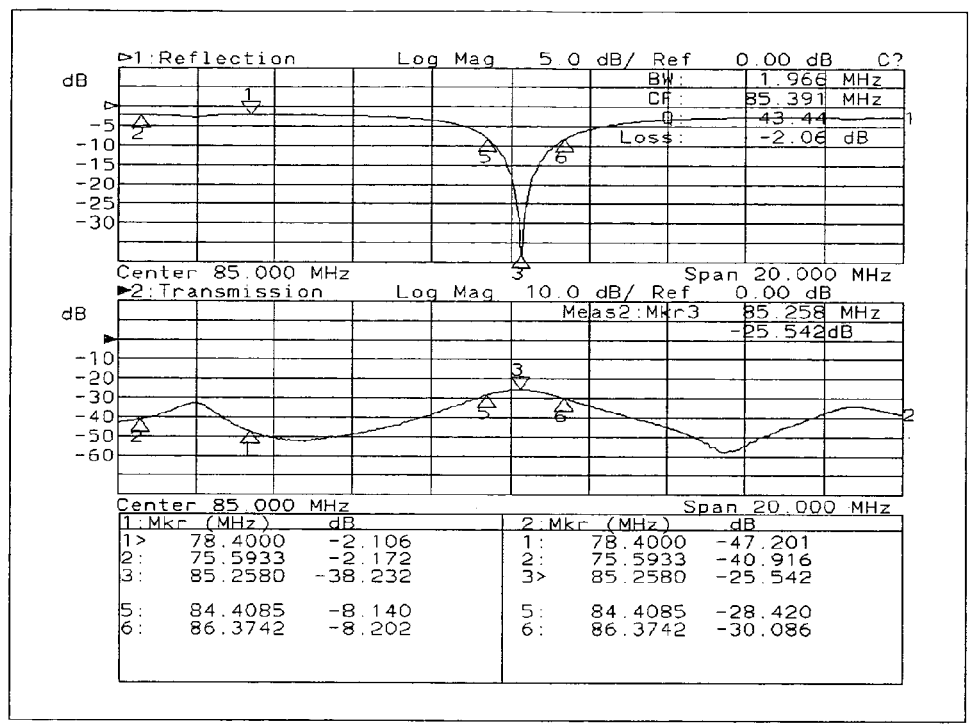
FIG. 9 (a-c) show screenshots of the measured S-parameters for Coil 3 connected to the reflection port, while Coil 1, Coil 2 and Coil 4 are (one after the other) being connected to the transmission port of an analyzer.
Figure 9B:
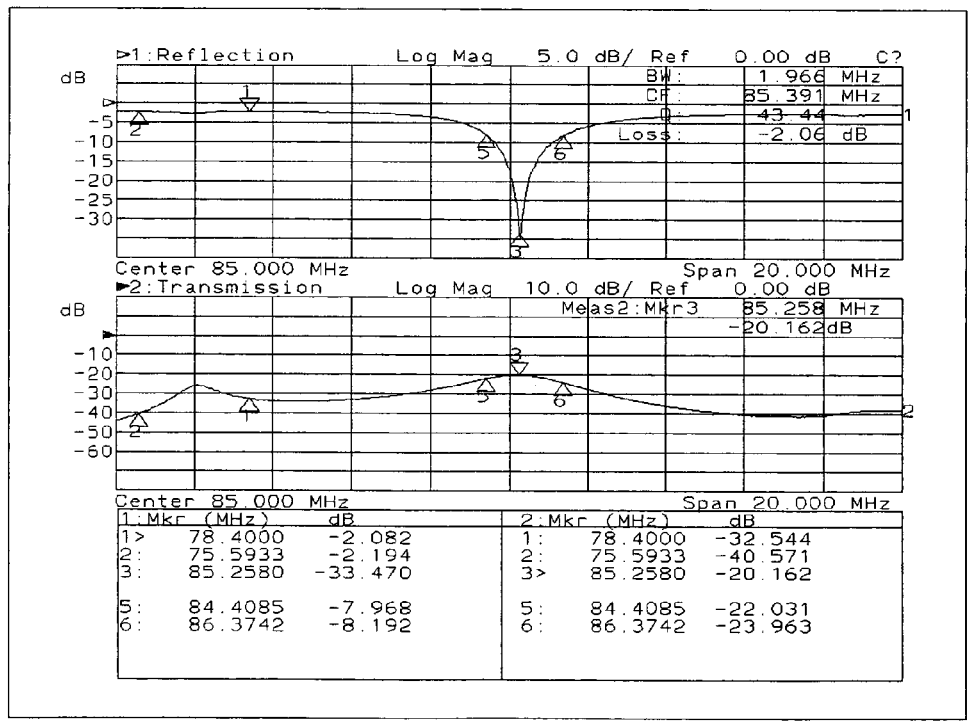
Figure 9C:
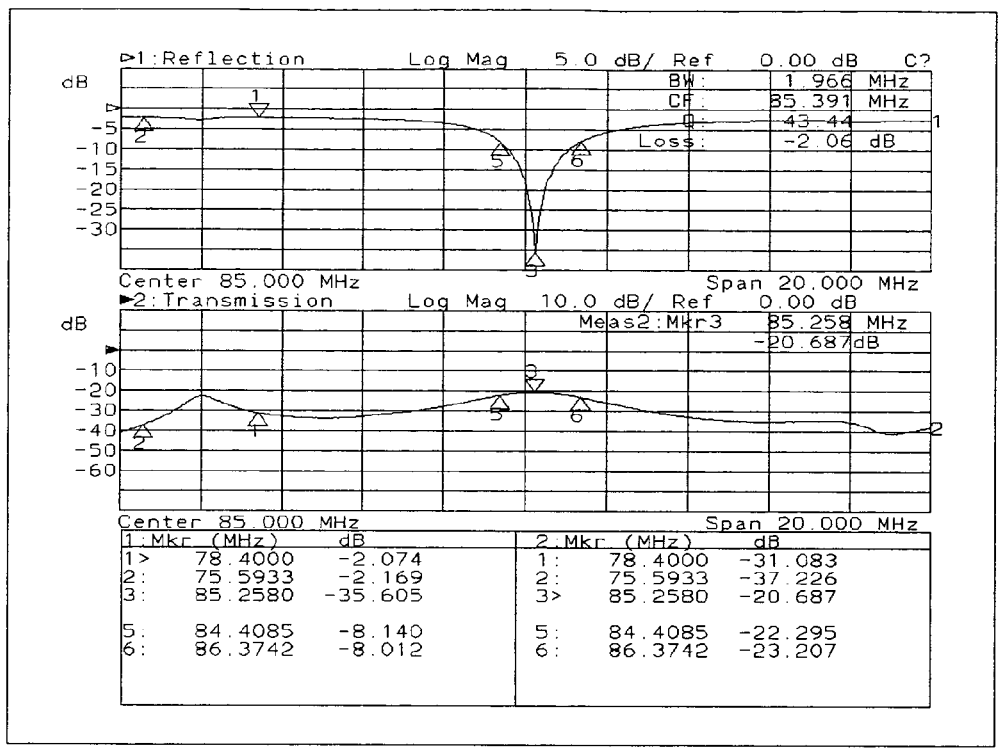
Figure 10A:
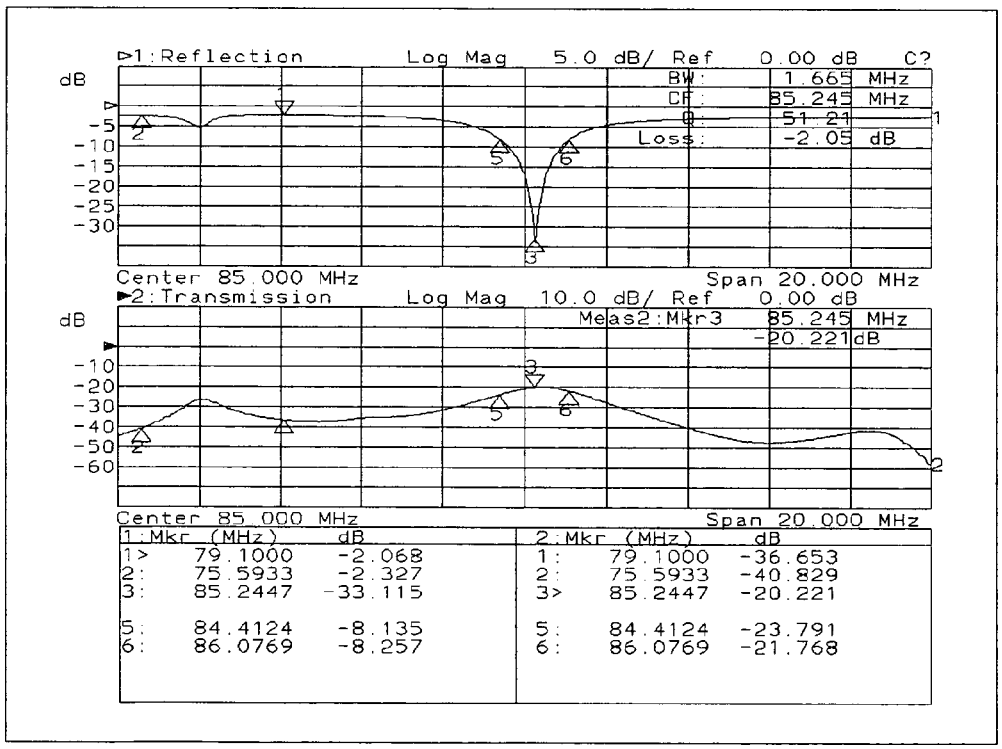
FIG. 10 (a-c) show screenshots of the measured S-parameters for Coil 4 connected to the reflection port, while Coil 1, Coil 2 and Coil 3 are (one after the other) being connected to the transmission port of an analyzer.
Figure 10B:
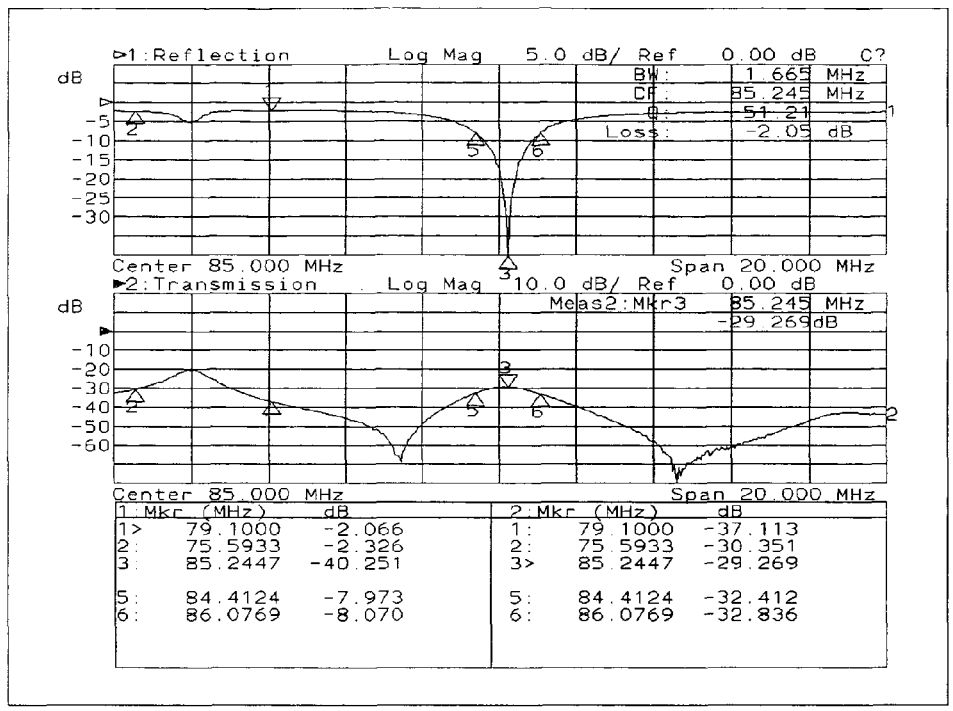
Figure 10C:
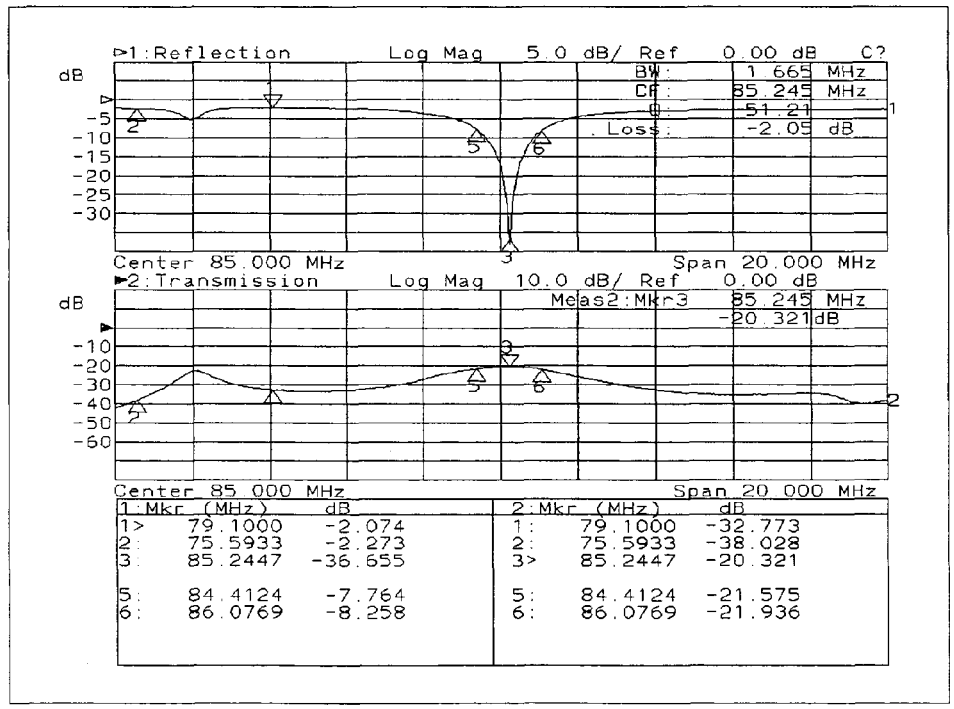

A prototype of the 4-element RPA-head coil 10 was constructed and is shown in FIG. 5. Apart from the additional baluns and active decoupling circuits, which switch the rotary head coil 10 into open circuit configuration during the transmission of the 90° RF pulse (via the built-in whole body RF system), the prototype RPA-head coil 10 is constructed in structure and dimensions accordingly to the method described in the previous section.

The decoupling circular conductor bases 8,9 and the counter wound inductor decoupling circuit 7 are fabricated on printed circuit board (PCB) and copper rod of 6 mm diameter is used for the main conductors 12. In a similar procedure as undertaken in the numerical simulation, an Agilent 2 port RF network analyser, model number 8712 ET is firstly used for tuning each coil 1,2,3,4 of the prototype rotary head coil 10 to 85 MHz and matching it to the system impedance of 50Ω. The tuning and matching is performed with the RPA-head coil 10 loaded with a spherical phantom having the same size and dielectric properties as modelled in the hybrid MoM/FEM simulation and is shown in FIG. 6.

Thereafter, the coupling between the counter-wound inductors is adjusted until mutual decoupling between coils 1,2,3,4 is achieved. This is determined by inspecting the measured S-parameters between coils. Shown in FIG. 7 to FIG. 10 are the measured S-parameters. The following table outlines the coil combinations for each measurement shown in the figures. In each case the measurement applies to the rotary phase array head coil 10 with a 2 Tesla field at 85 Mhz using 4 channels.

It will be noted that no "splitting" of the resonance frequency is visible; indicating the decoupling circuit as proposed herein, achieves mutually decoupling of coils 1,2,3,4.

| FIG. | S11 | S21 |
| --- | --- | --- |
| 7a | Coil 1 | Coil 2 |
| 7b | Coil 1 | Coil 3 |
| 7c | Coil 1 | Coil 4 |
| 8a | Coil 2 | Coil 3 |
| 8b | Coil 2 | Coil 1 |
| 8c | Coil 2 | Coil 4 |
| 9a | Coil 3 | Coil 1 |
| 9b | Coil 3 | Coil 2 |
| 9c | Coil 3 | Coil 4 |
| 10a | Coil 4 | Coil 1 |
| 10b | Coil 4 | Coil 2 |
| 10c | Coil 4 | Coil 3 |

Those skilled in the art will appreciate that for high field applications the coils 1,2,3,4, the counter-wound decoupling circuit 7 and interlaced decoupling base 14, may make use of distributed capacitors/inductors etched or machined using suitable RF-substrate materials. For low field strengths the elements of the RPA-head coil 10 are discrete elements.

Results

The prototype rotary head coil 10 was tested in a Bruker S200 2 T whole-body MRI system, equipped with four receiver channels. Two MRI experiments were undertaken to test the prototype RPA-head coil. In the first experiment, the RPA-head coil was loaded with a spherical phantom as shown in FIG. 6. The purpose of this first experiment is to show that the decoupling circuit can successfully decouple coils and to show that sensitivity deep at the centre is improved by the invention.

In the second experiment, a healthy male volunteer with consensual approval was imaged using the prototype RPA-head coil 10 and a commercially available 2 T receive-only quadrature birdcage coil. The objective of this second experiment was to demonstrate that, with improved sensitivity deep at the centre of the rotary head coil, the sum-of-squared composite brain image acquired by the RPA-head coil 10 achieves high homogeneity, comparable to brain images acquired using the birdcage coil. In addition, since the rotary head coil 10 is a phased array class of MRI RF-coil, parallel-imaging techniques can be used in conjunction with the RPA-head coil. A VD-GRAPPA parallel imaging reconstruction method is applied to demonstrate that parallel imaging is well suited and compliments the RPA-head coil 10. The GRAPPA method is described in our co-pending application referenced above.

Figure 11:
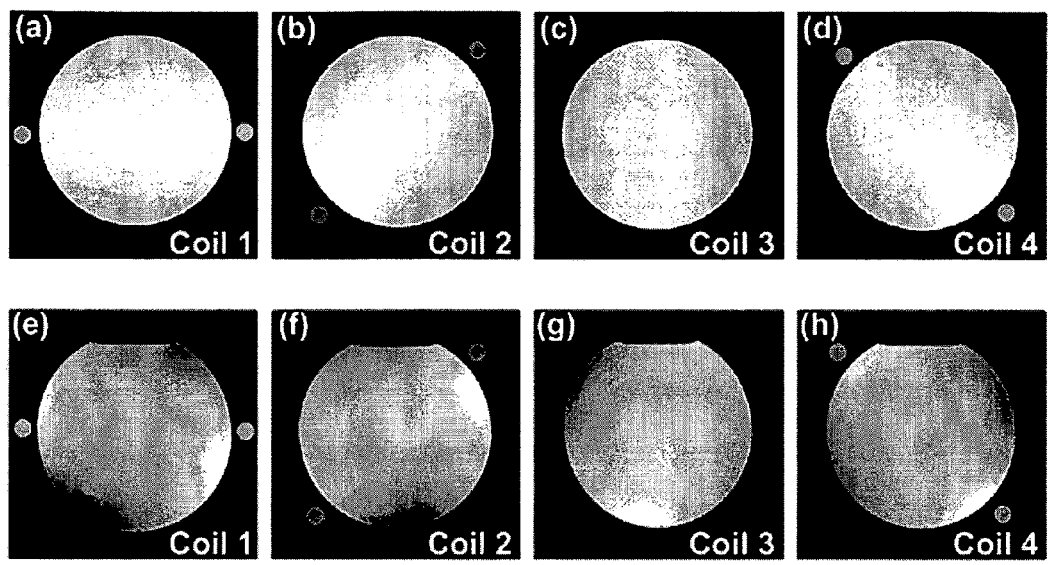
FIG. 11 (a-d) shows numerically calculated SI intensity corresponding to each coil element, and (e-h) shows four axial plane MR images of the spherical phantom acquired in parallel using the 4-element RPA head coil of FIG. 6.

Using a multi-slice-multi-echo pulse sequence with TR=1000 msec, TE=19.3 msec and NEX=1, 4 axial slices located at the mid section of the spherical phantom are acquired in parallel by each coil 1,2,3,4 of the RPA-head coil 10. Depicted in FIG. 11(*a*)-(d) are the hybrid MoM/FEM calculated SI profiles corresponding to each of the numerically decoupled coils 1,2,3,4, and in FIG. 11(*e*)-(h) are the experimental acquired MR images of the spherical phantom obtained from each individual decoupled coil of the constructed prototype RPA-head coil 10.

Figure 12:
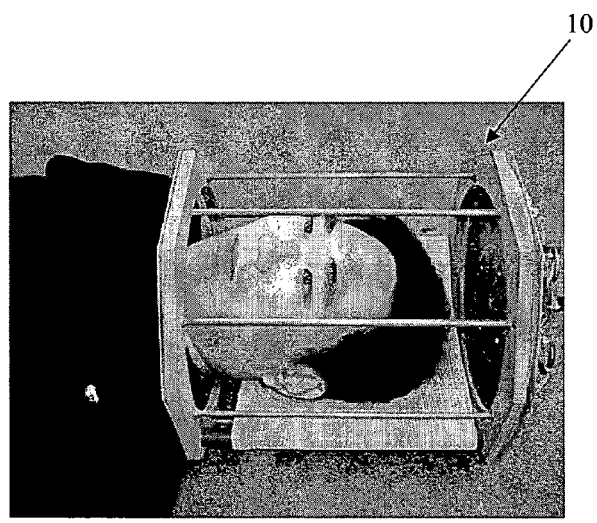
FIG. 12 shows a male volunteer with head rested inside the RPA head coil of FIG. 5.

The healthy male volunteer was firstly imaged with the constructed prototype RPA-head coil 10 and subsequently imaged with a commercial available 2 T receive-only quadrature birdcage coil. Shown it FIG. 12 is a photograph of the prototype RPA-head coil 10 loaded with the male volunteer.

Using a rapid acquisition with relaxation enhancement (RARE) imaging sequence, with TR=2000 ms, TE=91.65 ms and NEX=2, 4 axial slices located approximately at the eye level section of the male volunteer head are acquired in parallel by each coil element of the rotary phased array head coil. Depicted in FIG. 13(*a*)-(d) are the experimentally acquired MR brain images of the male volunteer corresponding to each coil 1,2,3,4.

Figure 13:
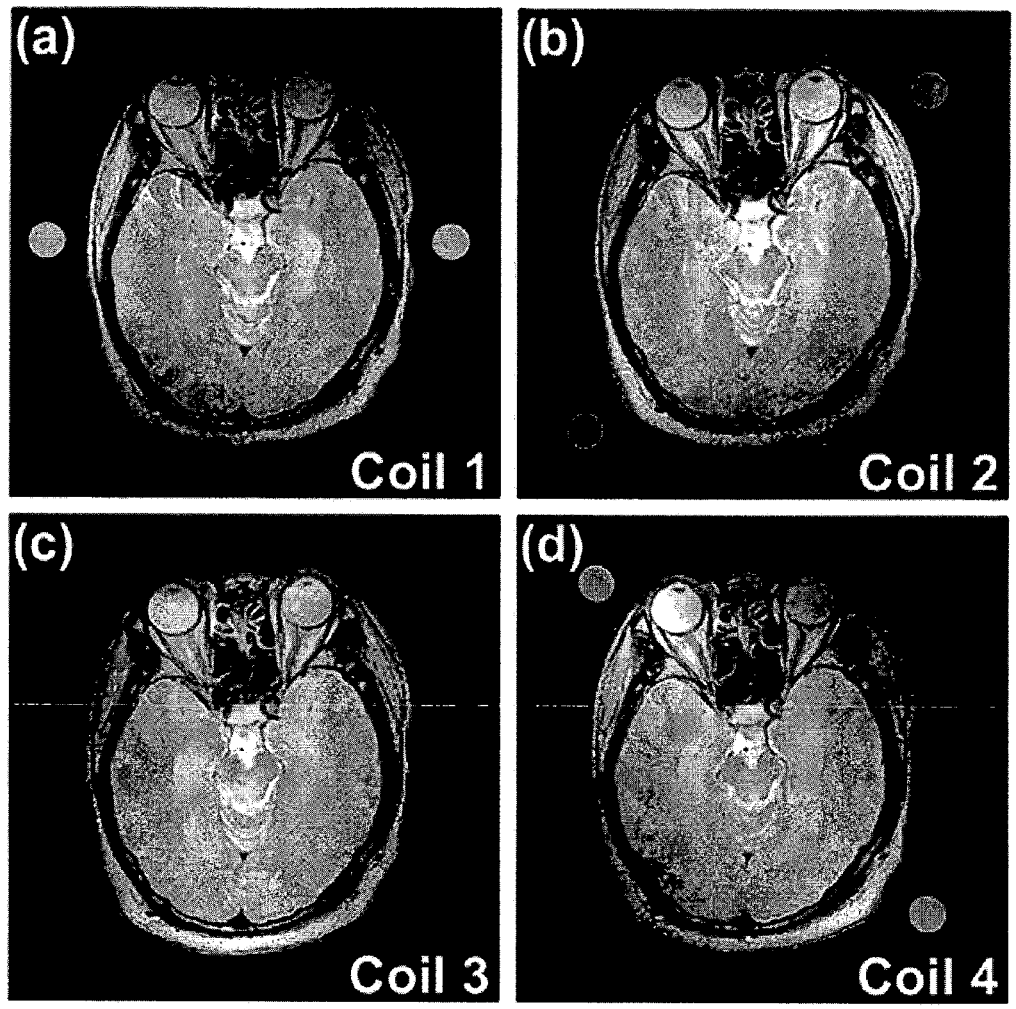
FIG. 13 shows four axial plane MR brain images acquired in parallel using the 4-element RPA head coil of FIG. 12.
Figure 14:
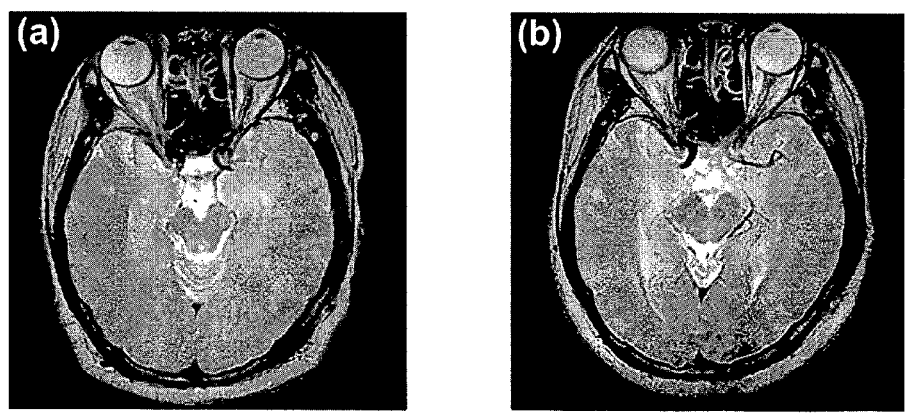
FIG. 14 (a) shows a composite brain image after applying a sum-of-square on the four brain images as shown in FIG. 13, and (b) shows an axial plane MR brain image acquired using a commercial available quadrature birdcage coil.

Using a sum-of-square method, the four brain images of FIG. 13 are combined together to form the composite brain image shown in FIG. 14(*a*). After completing the acquisition of the brain images using the prototype rotary head coil 10, the male volunteer was again imaged with a quadrature birdcage coil. The same imaging pulse sequence with similar imaging parameters is used. Depicted in FIG. 14(*b*) is the brain image acquired using a quadrature birdcage coil.

Given that the rotary head coil 10 is a class of phased array type of MRI RF coil, parallel imaging should be applicable with the rotary head coil. To show that parallel imaging can be used with the RPA-head coil 10, an off-line VD-GRAPPA parallel imaging reconstruction was undertaken. Detailed explanation on the operation of VD-GRAPPA had been reported in reference [Park et al, Magn Reson Med 53(1) pg 186-193, 2005]. A RARE imaging sequence, with TR=2000 ms, TE=91.65 ms and NEX=2 was firstly used for the acquisition of four full (256×256) complex k-space data of the volunteer brain in parallel, which were later decimated off-line for VD-GRAPPA reconstruction testing. In performing the off-line VD-GRAPPA parallel imaging sequence, two reduction factors of 4 and 2 were applied to all the four outer k-space data, which from the perspective of an actual k-space acquisition, will be similar to acquiring only a partial portion of the k-space data, thus achieving reduced scan time. 21 auto calibration signal (ACS) lines located at the central of the k-space were used to generate the complex weights required to reconstruct missing k-space lines of each coil. Shown in FIG. 15(*a*)-(d) is the four set of reduced k-space data with 21 ACS lines. Using a total number of 5 blocks, missing lines in each set of the reduced k-space were reconstructed. After Fourier transforming the fully VD-GRAPPA reconstructed k-space data, individual brain images corresponding to each individual coil 1,2,3,4 are shown in FIG. 15(*e*)-(h). Using a sum-of-square method, the four brain images of FIG. 15(*e*)-(h) are combined together to form a composite brain image and as shown in FIG. 15(*i*). For comparison purposes, shown in FIG. 15(*j*) is the composite brain image obtained from sum-of-squaring the four fully acquired k-space data.

SUMMARY

The decoupling circuit 7 proposed herein offer the advantages of optimising mutual decoupling without the restrictions inherent in traditional decoupling methods. The circuit 7 can be easily adapted for receive-only or transceive type of phased array coils and is especially suited for parallel imaging applications.

The decoupling circuit 7 has the advantage that it does not use any of the traditional decoupling methods such as the overlapping of coil elements, the use of low input impedance pre-amp and capacitor decoupling network, and hence may find new applications in future design of either receive-only or transmit and receive (transceive) types of MRI phase array systems.

Throughout the specification the aim has been to describe the invention without limiting the invention to any particular combination of alternate features.

The invention claimed is:

1. A decoupling circuit for an array of coil elements forming part of a Magnetic Resonance Imaging (MRI) phased array coil, the array of coil elements comprising:
   each coil element having a respective inductor;
   wherein counter wound inductors from adjoining coil elements of the array of coil elements are interlaced.

2. The decoupling circuit of claim 1, including current controlling capacitive circuitry.

3. The decoupling circuit of claim 1, wherein the inductance of each counter wound inductor is adjusted to achieve mutual decoupling between adjoining coil elements.

4. The decoupling circuit of claim 1, wherein the coil elements include main conductors which are equi-angularly spaced from the main conductors of adjoining coil elements.

5. The decoupling circuit of claim 1, wherein the array of coil elements forms part of one of a head coil, chest coil, extremity coil or whole body coil.

6. The decoupling circuit of claim 1, wherein the decoupling circuit forms part of a Magnetic Resonance Imaging (MRI) phased array coil.

7. The decoupling circuit of claim 1, wherein the decoupling circuit includes active detuning units.

8. A coil array system comprising an array of coil elements, the decoupling circuit of claim 1 and a decoupling base comprising two or more meandering conductor bases wherein main conductors of the coil elements share a common meandering conductor base and wherein the conductor bases are interlaced.

9. The coil array system of claim 8, wherein the conductor bases have inter-crossed capacitive networks at each crossover between the conductor bases.

10. The coil array system of claim 8, wherein the meandering conductor bases follow one of a generally circular, elliptical or rectangular path.

11. The coil array system of claims 8, wherein the coil array system is one of a head coil, chest coil, extremity coil or whole body coil.

12. A method of minimizing coupling between coil elements in a Magnetic Resonance Imaging (MRI) phased coil array system, the method including the steps of:
   connecting coil elements of the coil array system with a decoupling base of two or more meandering conductor bases wherein main conductors of the coil elements share a common conductor base;

incorporating counter wound inductors in a circuit of each coil element of the coil array system; and adjusting the inductance of each inductor until coupling between coil elements is minimised.

13. A decoupling base for an array of coil elements forming part of a Magnetic Resonance Imaging (MRI) phased array coil, comprising two or more meandering conductor bases, the coil elements having a respective main conductor wherein main conductors of the coil elements share a common meandering conductor base and wherein the respective meandering conductor bases are interlaced.

14. The decoupling base of claim 13, wherein the conductor bases have inter-crossed capacitive networks at each cross-over between the conductor bases.

15. The decoupling base of claim 13, wherein the meandering conductor bases follow one of a generally circular, elliptical or rectangular path.

16. The decoupling base of claim 13, wherein the decoupling base forms part of one of a head coil, chest coil, extremity coil or whole body coil.

* * * * *